United States Patent [19]

Bilstad et al.

[11] Patent Number: 4,501,531

[45] Date of Patent: Feb. 26, 1985

[54] CONTROL CIRCUIT FOR A BLOOD FRACTIONATION APPARATUS

[75] Inventors: Arnold C. Bilstad, Deerfield; John T. Foley, Wheeling, both of Ill.

[73] Assignee: Baxter Travenol Laboratories, Inc., Deerfield, Ill.

[21] Appl. No.: 557,818

[22] Filed: Dec. 5, 1983

Related U.S. Application Data

[62] Division of Ser. No. 330,898, Dec. 15, 1981, Pat. No. 4,447,191.

[51] Int. Cl.³ .............................................. F04B 49/00
[52] U.S. Cl. ........................................ 417/63; 340/502;
340/691; 604/67; 604/123
[58] Field of Search ......................... 604/50, 51, 4–6,
604/122, 123, 65–67, 131, 151, 245–247;
128/DIG. 12, DIG. 13; 417/12, 63, 44, 45;
340/691, 502

[56] References Cited

U.S. PATENT DOCUMENTS

| 3,618,082 | 11/1971 | Feulner ........................... 340/502 X |
| 3,648,694 | 3/1972 | Mogos et al. . |
| 3,686,654 | 8/1972 | Judlowe ............................. 340/502 |
| 3,688,294 | 8/1972 | Erpelding ........................... 340/502 |
| 3,735,043 | 5/1973 | Riethmeier et al. ............ 340/502 X |
| 3,812,482 | 5/1974 | Clark . |
| 3,946,731 | 3/1976 | Lichtenstein . |
| 3,984,825 | 10/1976 | Fujita ................................. 340/502 |
| 4,086,924 | 5/1978 | Latham, Jr. . |
| 4,111,198 | 9/1978 | Marx et al. . |
| 4,171,185 | 10/1979 | Duke et al. . |
| 4,185,629 | 1/1980 | Cullis et al. . |
| 4,210,138 | 7/1980 | Jess et al. . |
| 4,217,993 | 8/1980 | Jess et al. . |
| 4,227,526 | 10/1980 | Goss . |
| 4,277,226 | 7/1981 | Archibald . |

FOREIGN PATENT DOCUMENTS

WO81/02979 10/1981 PCT Int'l Appl. .

Primary Examiner—Edward K. Look
Attorney, Agent, or Firm—Paul C. Flattery; Daniel D. Ryan; Eugene M. Cummings

[57] ABSTRACT

An apparatus for the continuous flow fractionation of whole blood incorporates motor driven whole blood, anti-coagulant and replacement pumps, negative and positive pressure monitors, and a dual bubble detector which function in conjunction with a disposable single-use flow system and a hollow fiber filter to separate and collect plasma from whole blood. Operation of the pump motors, pressure monitors and bubble detector is controlled by a control circuit within the apparatus to provide one of several operator-selected operating modes, including run, prime and reinfuse modes. The control circuit provides an alarm which can be cancelled by the operator when certain system parameters fall outside of normal operating limits, and interrupts operation of the pumps when the parameters exceed maximum limits. A failsafe circuit independent of the control circuits interrupts power to the pump motors in the event the motors do not stop upon detection of a bubble or fluid absence in the flow system.

9 Claims, 12 Drawing Figures

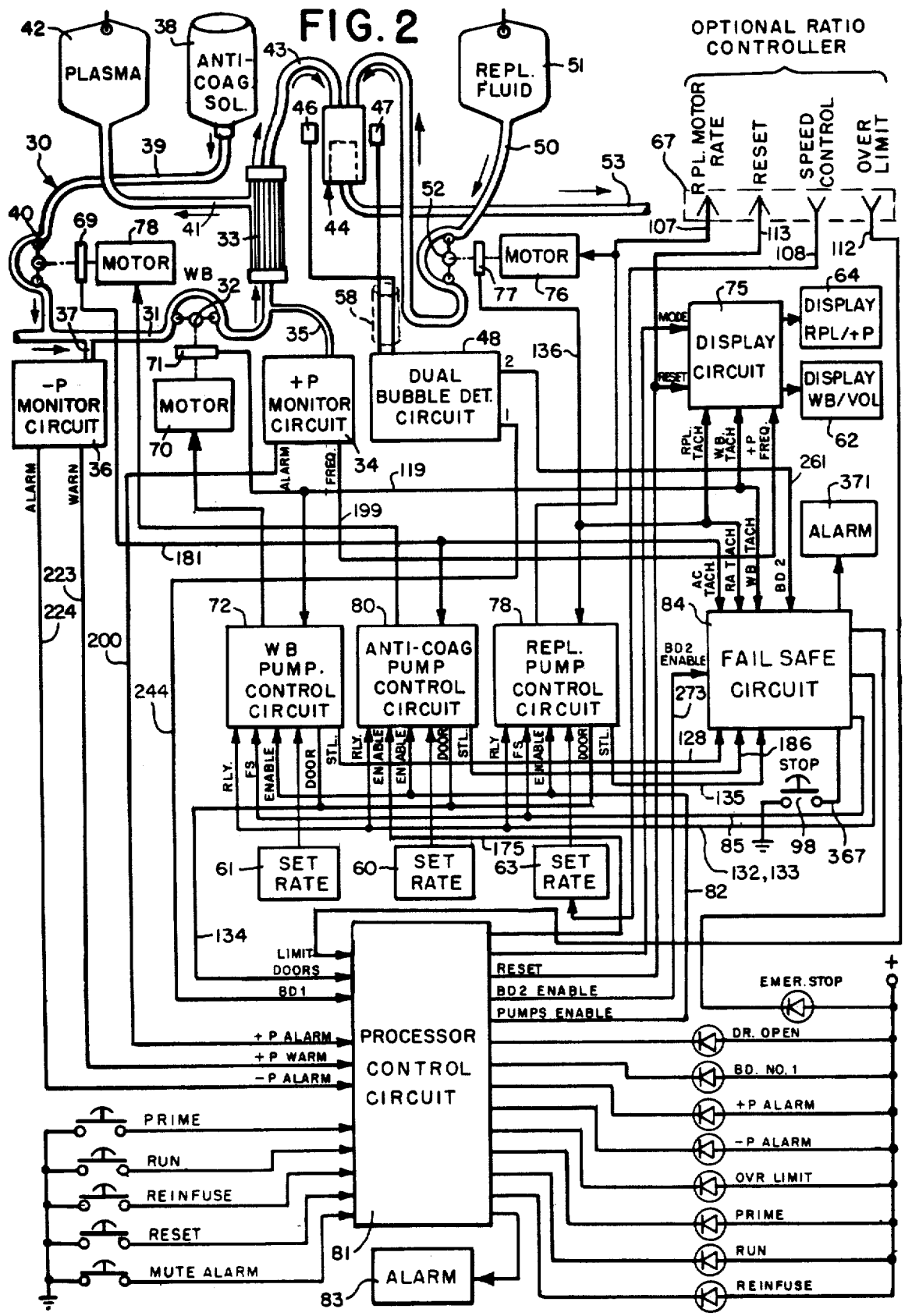

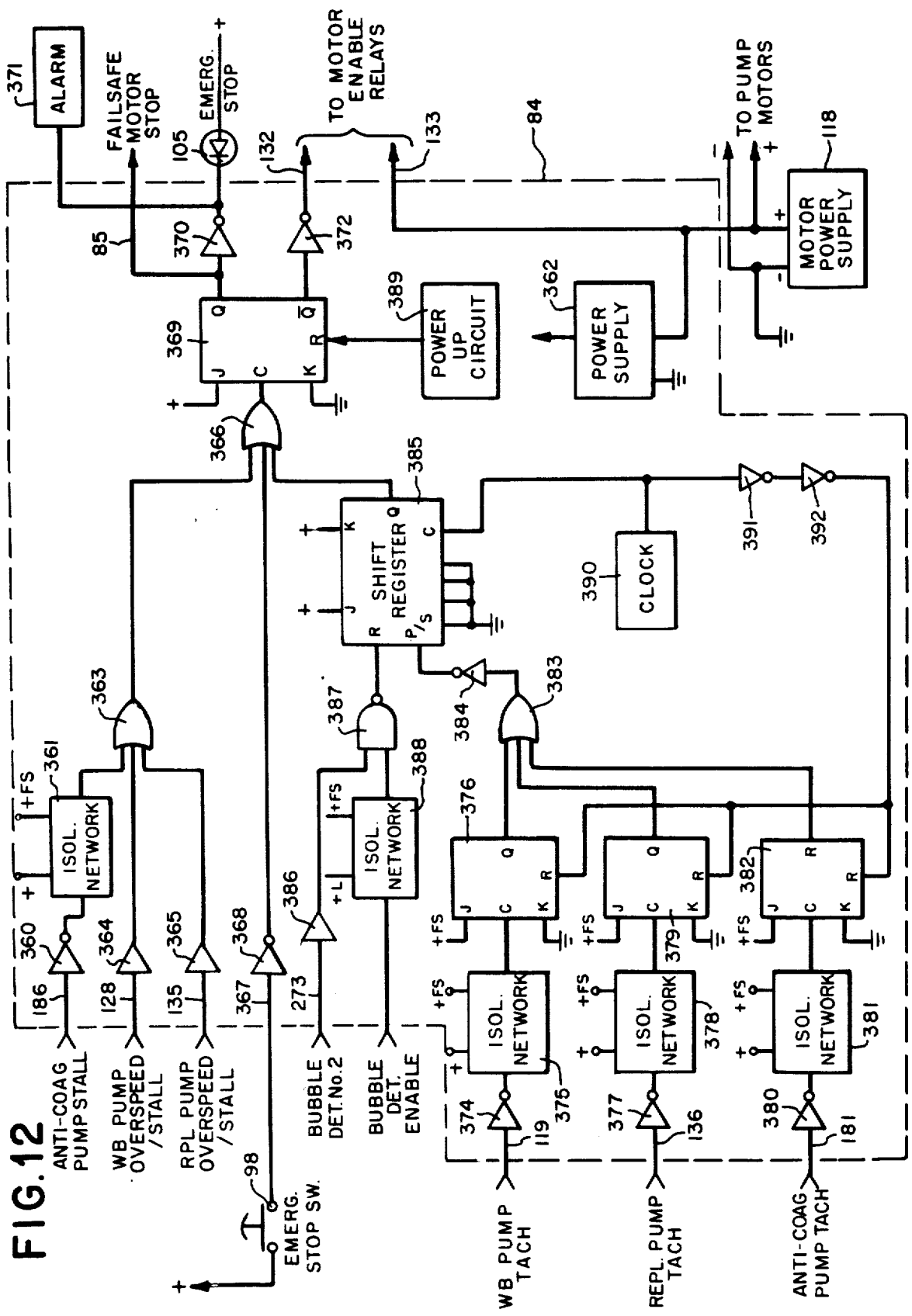

No. 4,501,531

CONTROL CIRCUIT FOR A BLOOD FRACTIONATION APPARATUS

This is a division of application Ser. No. 330,898 filed Dec. 15, 1981, now U.S. Pat. No. 4,447,191.

BACKGROUND OF THE INVENTION

The present invention relates generally to apparatus for processing whole blood, and more specifically to blood fractionation apparatus for separating and collecting a desired blood component, such as plasma.

Various methods and apparatus have been developed for the continuous flow processing of whole blood, wherein whole blood is taken from a live donor, a desired blood component is separated and collected, a replacement fluid is added to the processed blood, and the processed blood is returned to the donor. Blood components typically collected using such processing include plasma (plasmapheresis), white blood cells (leukopheresis) and platelets (plateletpheresis).

Continuous flow blood processing apparatus maybe of the centrifugal type, wherein the differing density of the collected blood component causes the component to congregate for collection at a particular radial distance in a centrifuge, or may be of the filter type, wherein the particle size of the collected component allows only that component to pass through a filter membrane into a collection chamber. Filter type apparatus is generally preferable for continuous flow plasmapheresis applications, since such apparatus does not require complex rotating machinery and is more compact and less costly to manufacture.

One form of filter which is particularly attractive for use in plasmapheresis apparatus utilizes a plurality of parallel microporous hollow fibers arranged side-by-side in the form of a bundle within a hollow cylinder. As whole blood is caused to flow through the fibers the plasma component passes through the walls of the fibers to the surrounding container, which forms a collection chamber from which the component is transported to a collection bag. A preferred construction and method of manufacture of such a hollow fiber filter is shown in the copending application of Robert Lee and William J. Schnell, entitled, "Microporous Hollow Fiber Membrane Assembly and Its Method of Manufacture", Ser. No. 278,913, filed June 29, 1981.

To preclude operation in the event of a mechanical malfunction, the plasmapheresis apparatus typically includes a plurality of devices which monitor the fluid flow system. One such device may be a bubble detector of either the light or ultrasonic type which monitors a particular segment of the tubing for fluid absence, such as might result from a bubble or air in the system. Another such monitor device monitors for either excessive negative pressure at the inlet of the system or to excessive positive pressure downline of the whole blood pump.

In the operation of plasmapheresis apparatus it is necessary that the apparatus operate in various modes, including a purge mode for displacing air from the system, a run mode for performing the plasmapheresis process, and a reinfuse mode for returning fluid to the patient. The apparatus therefore requires a control system which allows the selection of these modes quickly and without undue attention on the part of the operator. The control circuit should include necessary interlocks to prevent inadvertent mis-selection of an operating mode, and should condition all elements of the processing apparatus, including the bubble detector and pressure monitoring devices.

The plasmapheresis apparatus should also include a failsafe control circuit independent of the control circuit which monitors all functions and removes power from the pump motors when a stop is called for by the control circuit and not responded to by the pump motor.

The present invention provides control systems for blood fractionation apparatus such as that utilized for plasma separation and collection wherein a user-cancellable audible alarm is provided for a first category of system parameters, a non-cancellable visual alarm and interruption of operation are provided for a second category of parameters, and wherein the operating mode and the operation of the pumps are continuously and independently monitored and operation of the system is terminated after a predetermined delay in the event of an uncorrected malfunction.

In addition, the plasmapheresis apparatus described herein provides for convenient connection of an auxiliary collection monitoring and replacement fluid ratio control apparatus such as that described in the copending applications of Arnold C. Bilstad and John T. Foley, entitled, "Blood Fractionation Apparatus Having Collected Volume Display System", Ser. No. 330,899; "Blood Fractionation Apparatus Having Collection Rate Display System", Ser. No. 330,901; and "Blood Fractionation Apparatus Having Replacement Fluid Ratio Control System", Ser. No. 330,900; all assigned to the present assignee and filed concurrently herewith. As described in these applications this apparatus provides an exchange mode wherein an operator-selected ratio between the volume of plasma collected and the volume of replacement fluid added is automatically maintained; and an autologous mode wherein the replacement pump is connected to withdraw fluid from the collection container for secondary processing and return to the donor, and the operating rate of the pump is automatically varied to maintain a constant plasma level in the collection container.

SUMMARY OF THE INVENTION

The invention is directed, in a blood fractionation apparatus operable in conjunction with a disposable fluid flow system for separating and collecting a blood fraction from whole blood, and including at least one motor-driven pump for conveying blood through the flow system, and a monitoring device providing an alarm output in response to an abnormal condition in the system, to a control system comprising a flip-flop responsive to a momentary alarm output from the monitoring device for producing a first alarm control signal indicative of the occurrence of the alarm, a latch register responsive to the occurrence of the control signal for producing a second alarm control signal indicative of the alarm upon application of a latch control signal, aural alarm means, and visual alarm means. The control system further comprises alarm control circuit means responsive to the first alarm control signal for activating the aural and visual alarm means, and responsive to the second alarm control signal for inhibiting only the aural alarm means; and user-actuated switch means for applying a latch control signal to the latch register to cancel the aural alarm without cancelling the visual alarm.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 2 is a functional block diagram partially in schematic form showing the principal components of the plasmapheresis apparatus of FIG. 1.

FIG. 12 is a simplified schematic diagram partially in functional block form of the failsafe control system of the plasmapheresis apparatus of FIG. 1.

DESCRIPTION OF THE PREFERRED EMBODIMENT

Figure 1:
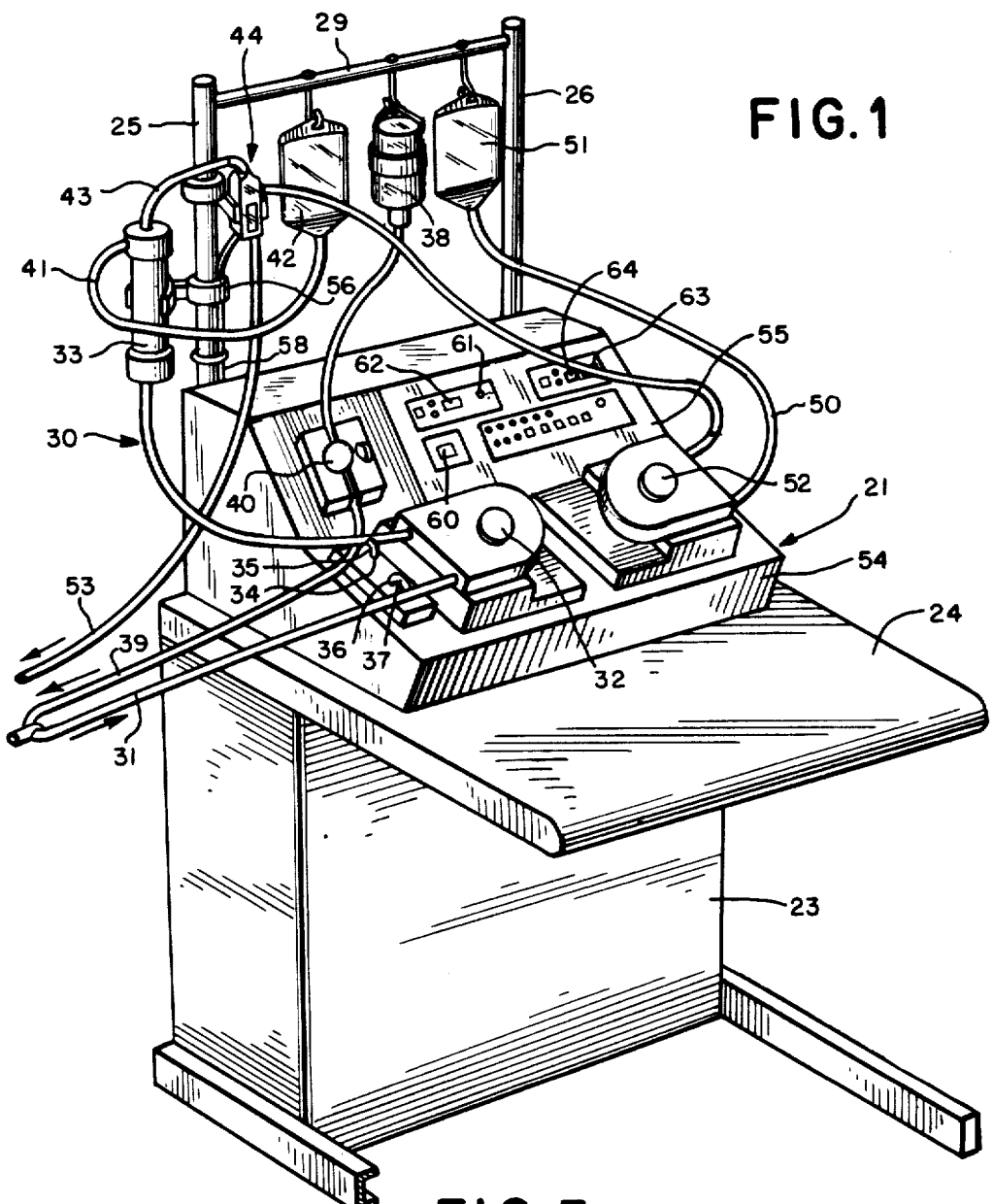
FIG. 1 is a perspective view of plasmapheresis apparatus incorporating a control system constructed in accordance with the invention.

Referring to the drawings, and particularly to FIG. 1, a plasmapheresis apparatus 20 incorporating the present invention is seen to include a table-mounted processor unit 21 mounted on a pedestal 23 of conventional design having a generally horizontal top surface 24 on which the processor unit is supported. It will be appreciated that the processor unit may be removed as necessary from table 21 and installed on other surfaces. The apparatus preferably includes a pair of vertical support poles 25 and 26 attached to the rear surface (not shown) of the processor unit. A horizontal bar 29 may be provided between the two support rods to allow a plurality of collection and dispensing containers of conventional construction to be hung by means of appropriate hangers.

The processing apparatus 20 operates in conjunction with a fluid circuit generally identified by the reference numeral 30 in FIG. 1 and shown schematically in FIG. 2. The fluid circuit 30 includes a plurality of flexible plastic tube segments which form fluid conduits between various components of the fluid circuit. As shown in FIG. 2, whole blood derived from a donor is conveyed through a first tubing segment 31 and a peristaltic-type whole blood (WB) pump 32 to a hollow fiber-type filter 33 mounted on support rod 25. The operation of the WB pump is monitored by a positive pressure (+P) monitor circuit 34 connected to tubing segment 31 downline of the WB pump by a tubing segment 35. Negative pressure, such as might occur upon the collapse of a vein, is monitored for by means of a negative pressure (−P) monitor circuit 36 connected to tubing segment 31 upline of the WB pump 32 by a tubing segment 37.

To prevent blood from clotting while in process in the apparatus anticoagulant solution from a supply container 38 is introduced at the point of blood withdrawal through a tubing segment 39. A peristaltic-type pump 40 is provided along tubing segment 39 to provide a controlled rate of addition of the anticoagulant fluid to the whole blood.

Plasma separated from the whole blood within the hollow fiber filter 33 is conveyed by a tubing segment 41 to a plasma collection container 42. The pressure provided by WB pump 32 is sufficient to cause flow from the filter to the collection container. The plasma-deficient processed blood from filter 33 is conveyed through a tubing segment 43 to an ultrasonic bubble detector 44, which may be similar in structure and operation to that described in the copending application of Arnold C. Bilstad and Michael Wicnienski, entitled, "Liquid Absence Detector", Ser. No. 127,552, filed Mar. 6, 1980. Basically, this bubble detector 44 includes a hollow housing having an internal filter screen assembly 45. Any bubbles in the processed blood fluid collect at the upper portion of the housing. An ultrasonic sound transmitter 46 and an ultrasonic sound receiver 47 positioned at opposite sides of the upper portion of the housing detect bubble formation. The source 46 and detector 47 are connected to a dual bubble detector circuit 48 which provides first and second independent outputs upon the occurrence of a bubble or liquid absence.

Replacement fluid is added to the plasma-deficient blood at this location through a tubing segment 50 which is connected at one end to a replacement fluid container 51 and at its other end to the housing of bubble detector 44. A peristaltic-type replacement pump 52 is positioned along tubing segment 50 to establish a controlled flow rate for the replacement fluid. The combined plasma-deficient whole blood and replacement fluid are pumped from bubble detector 44 back to the donor through a tubing segment 53.

As shown in FIG. 1, the plasmapheresis apparatus 20 is housed in a cabinet 54 which includes a sloped upper portion on which a control panel 55 and the anticoagulant pump 40 are located. The cabinet also includes a sloped lower portion on which the WB pump 32 and replacement pump 52 are mounted, together with the inlet to the positive pressure monitor 34 and the inlet to the negative pressure monitor 36. When flow system 30 is installed on the plasmapheresis apparatus, the anticoagulant supply container 38, replacement fluid source container 51 and plasma collection container 42 are suspended from the horizontal support bar 29 as shown, and the hollow fiber filter 33 is mounted by means of an appropriate mounting bracket 56 to vertical support rod 25. The bubble detector 44 is similarly mounted to support rod 25 by means of a mounting bracket 57, and the ultrasonic source 46 and detector 47 thereof are electrically connected to the processor housing by an electrical cable 58.

Control panel 55 includes operator-actuated controls for operating the plasmapheresis apparatus. These include a selector switch 60 by which the operating speed of the anticoagulant pump 40 is set, a potentiometer control 61 and digital readout 62 by which the operating speed of the WB pump 32 is controlled, and a potentiometer 63 and digital readout 64, by which the operating speed of the replacement pump 52 is controlled. A plurality of pushbutton switches 65 are provided to establish the operating mode of the apparatus, and a plurality of status-indicating lights 66 provide indications of malfunctions in the system. A connector 67 (FIG. 2) on the back panel of the processor enables an auxiliary collection monitoring and replacement fluid ratio control apparatus as previously described to be readily connected.

Referring to FIG. 2, the whole blood pump 32 is driven by a motor 70 having a mechanically coupled tachometer 71. Power for operating motor 70 is provided by a motor control circuit 72 which responds to rate setting means in the form of potentiometer control 63 and a tachometer feedback signal from the tachometer 71 to maintain a desired motor operating speed. The actual pump flow rate is displayed by readout 62 as part of a display circuit 75 which receives the tach output signal from tachometer 71.

Similarly, the replacement pump assembly 52 is driven by a motor 76 having an associated tachometer 77. Power for motor 76 is provided by a motor control circuit 78 which responds to a tach feedback signal from tachometer 77 and the rate selected by the panel-mounted potentiometer 63 to maintain a desired constant motor speed. The actual pump flow rate is displayed by readout 64 as part of the display circuit 75.

The anticoagulant pump 40 is driven by a stepper motor 78. Drive signals for motor 79 are developed by a motor control circuit 80 which responds to rate selection switch 60 to maintain a desired anticoagulant flow rate. A tachometer associated with motor 79 provides tach pulses for use by other circuits of the apparatus.

The operation of the various pump motors is controlled by a processor control circuit 81 which includes five mode select pushbuttons 66 on front panel 55. System malfunctions, such as negative pressure at pressure monitor 36, or excessive positive pressure at pressure monitor 34, or the occurrence of a bubble or other fluid absence as signaled at the first output (BD1) of bubble detector circuit 48, result in the application of a signal to processor control circuit 81. This circuit responds by producing a control signal on a first motor control line 82 to the motor control circuits 72, 78 and 80 to interrupt operation of the motors. In addition, an alarm 83 associated with the processor control circuit may be sounded and an appropriate one of indicator lamps 66 may be lit to alert the operator.

The plasmapheresis apparatus 20 further includes a failsafe control circuit 84 which functions to remove power from the pump motors in the event that processor control circuit 81 fails to respond to a system malfunction. To this end, the outputs of the motor tachometers are applied to the failsafe circuit, together with the second output (BD2) of bubble detector 48. Upon the occurrence of a bubble or fluid absence, as signaled by bubble detector circuit 48, failsafe circuit 84 determines from the simultaneously applied tach output signals whether the pump motors have in fact stopped and, if motion is detected after a period of time, provides an additional stop signal which removes motor operating power to motor control circuits 72 and 78 on a second motor control line 85.

Figure 3:
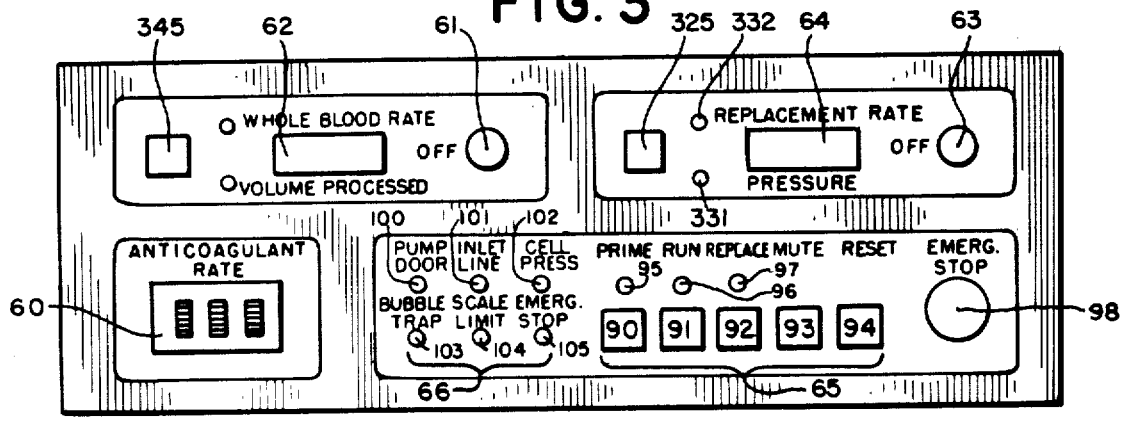
FIG. 3 is an enlarged front elevational view of the control panel of the plasmapheresis apparatus of FIG. 1.

Referring to FIG. 3, operator designation of the operating mode of plasmapheresis apparatus 20 is accomplished by five push button switches 90–94 which are mounted on control panel 55 and which designate prime, run, reinfuse, mute and reset operating instructions, respectively. Operation in the prime, run and reinfuse modes is indicated by indicator lamps 95–97, respectively. An emergency stop switch 98 associated with failsafe circuit 84 provides an additional means of stopping the apparatus in an emergency. The occurrence of a abnormal condition such as an emergency stop, a pump door being opened, a bubble being detected, limits being exceeded by either the positive pressure or negative pressure monitors, or a ratio being exceeded by an auxiliary collection monitor and ratio control apparatus (if installed), is indicated by indicator lamps 100–105 on control panel 55.

Figure 4:
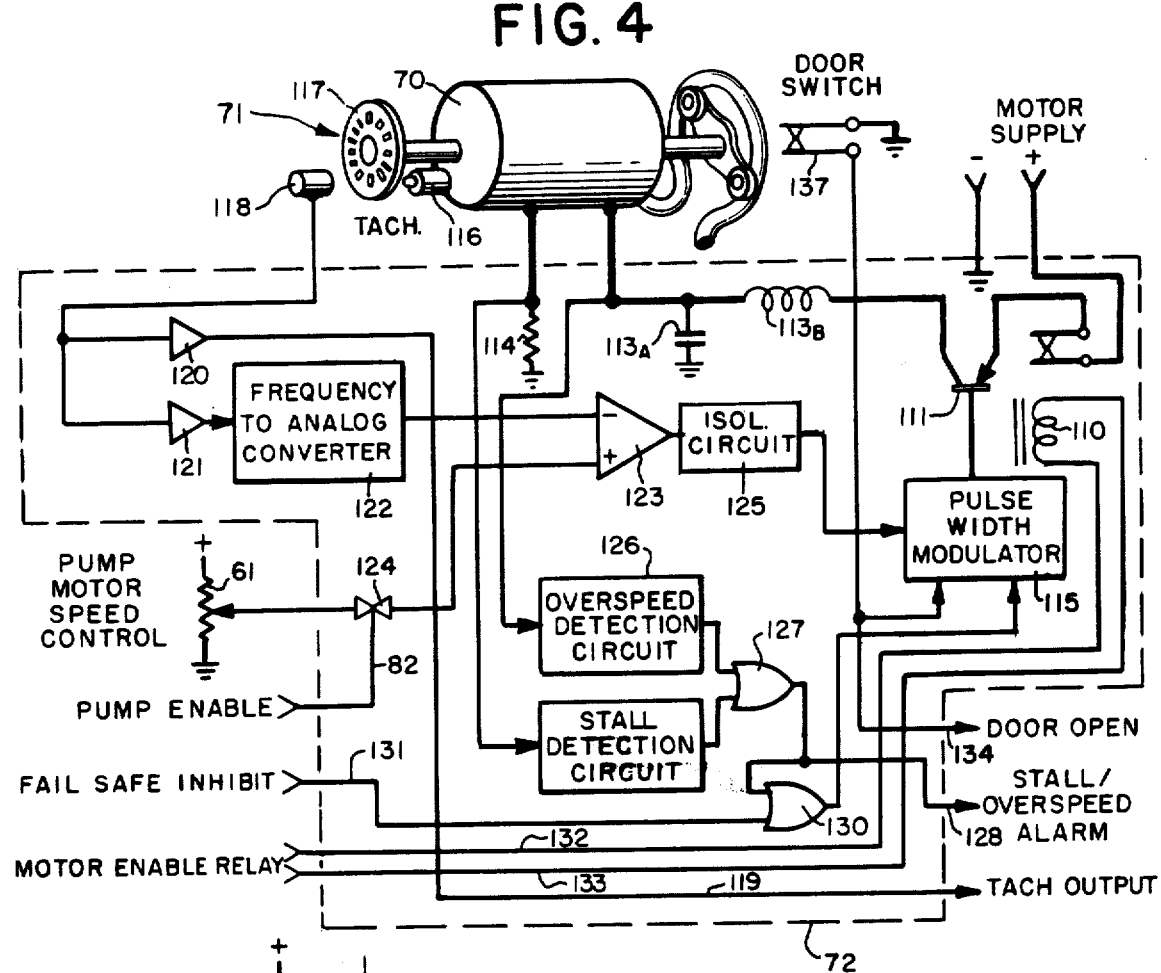
FIG. 4 is a functional block diagram partially in schematic form of the whole blood pump motor control circuit of the plasmapheresis apparatus of FIG. 1.

Referring to FIG. 4, operating power is supplied to the WB pump motor 70 through a motor control circuit 72 comprising the normally open contacts of a motor control relay 110, a series-connected power transistor 111, and a reactance control network comprising a series-connected inductance 113B and a shunt-connected capacitor 113A. The series combination of these components supplies power from a unidirectional motor current source (not shown in FIG. 4) to the motor. The return line from the motor includes a series-connected current metering resistor 114.

Pump motor 70 is a direct current type motor and receives excitation over a variable duty cycle through power transistor 111. The conduction of this transistor is controlled by excitation control means in the form of a pulse width modulator 115 which provides an appropriate control signal to the base electrode of the transistor.

Tachometer 71, which is seen to include a light source 116, a slotted disc 117 and a photodetector 118, operates in a conventional manner to provide output pulses indicative of incremental rotation of the pump motor. These pulses are applied to a first amplifier 120 wherein they are amplified for use by other systems within the plasmapheresis apparatus, and to a second amplifier 121 wherein they are amplified for application to a frequency to analog converter circuit 122. This circuit develops an analog output signal amplitude-dependent on the frequency of the tach pulses. This signal is applied to the inverting input of a comparator amplifier 123, wherein it is compared with a speed control signal applied to the non-inverting input from potentiometer 61 through an analog switch device 124. The control gate of switch device 124 is connected to the first pump control line 82 so that in the absence of an appropriate output signal from control circuit 81 enabling the motor no reference signal is applied to the non-inverting input of comparator 123.

Comparator amplifier 123 operates in a conventional manner to produce an output signal indicative of the difference between its inputs. This differential signal is applied through an isolation circuit 125 to pulse width modulator 115, wherein it controls the duty cycle of power transistor 111, and hence the speed of pump motor 70.

By reason of the action of comparator 123 in comparing the speed-dependent tach signal with the operator-set reference signal from potentiometer 61, a closed loop system is formed whereby motor 70 is maintained at an operator-designated speed. Any change in pump speed tending away from the designated speed is automatically compensated for by a corresponding correction in the duty cycle of transistor 110.

To provide protection against overspeed operation, the excitation level applied to pump motor 70 is continuously monitored by an overspeed detection circuit 126. In the event of an overspeed condition, this circuit produces an output which is coupled through an OR gate 127 to an alarm output bus 128, and through OR gate 127 and a second OR gate 130 to the inhibit input of pulse width modulator 115, wherein it prevents the application of current to the base of transistor 111, thereby stopping the motor.

The remaining input of OR gate 130 is connected to a failsafe inhibit line 131 connected to the failsafe control line 85 of the plasmapheresis apparatus. Application of an inhibit signal to this control line by failsafe circuit 84 results in pulse width modulator 115 being inhibited. Additional protection against uncontrolled operation of pump motor 70 is provided by relay 110. This relay must be energized through a pair of relay control lines 132, 133 in order for the pump motor 70 to receive operating power. As will be seen presently, the presence of an enabling control signal on these lines is dependent on the failsafe control system 84 of the apparatus.

As an additional safety measure, WB pump 32 has associated with it a door switch 137 which provides an open circuit in the event the pump door is opened. This contact action is used to inhibit pulse width modulator 115 to prevent further operation of the pump, and provide an output on a door open line 134 to control circuit 81.

Figure 5:
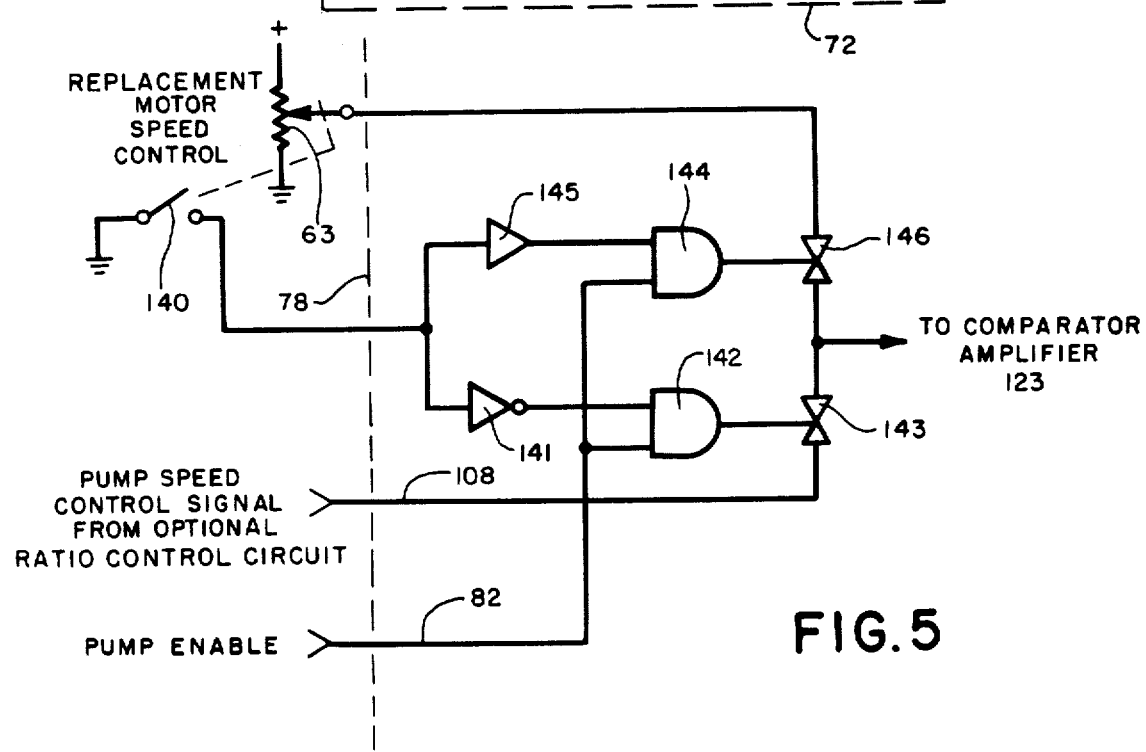
FIG. 5 is a simplified schematic diagram of a portion of the motor control circuit of FIG. 4 showing an alternative input circuit for use therein to adapt the circuit for use in conjunction with the replacement pump motor.

An alternative input circuit which allows the WB pump motor control circuit 72 to function as the replacement pump motor control circuit 78 is shown in FIG. 5. As seen in FIG. 2, the replacement pump motor circuit 78, in the manner of motor control circuit 72, produces a stall/overspeed alarm on a control line 135 and provides a motor tach output signal on a control line 136. Also, pump control circuit 78 receives inputs from the pump enable line 82, the failsafe inhibit line 85, and the failsafe motor enable relay lines 132, 133.

The replacement pump rate control potentiometer 63 includes a switch 140 which is closed upon the potentiometer being turned to its minimum rate fully counterclockwise position. This causes an enabling signal to be applied through an inverter amplifier 141 to a first AND gate 142, thereby allowing a pump enable control signal on line 82 to be applied through gate 142 to the gate electrode of a first analog switch device 143. This enables switch 143 and allows an analog pump speed control signal developed by the previously described optional collection rate and replacement fluid ratio control apparatus to control the speed of replacement pump motor 76. At the same time, the closure of contact 140 results in a second AND gate 144 being inhibited through a non-inverting amplifier 145, thereby preventing the enabling signal on line 82 from conditioning a second analog switch device 146 in series with the arm of potentiometer 63 to a conductive mode.

When the optional replacement fluid rate control apparatus is not connected or is not in use, potentiometer 63 is positioned mid-range and switch 140 is open. This results in analog switch device 146 being enabled so that motor speed is determined by the position of the arm on potentiometer 63. At the same time, analog switch device 143 is inhibited, and analog control signals from the option, if present, have no effect on the speed of the motor.

Figure 6:
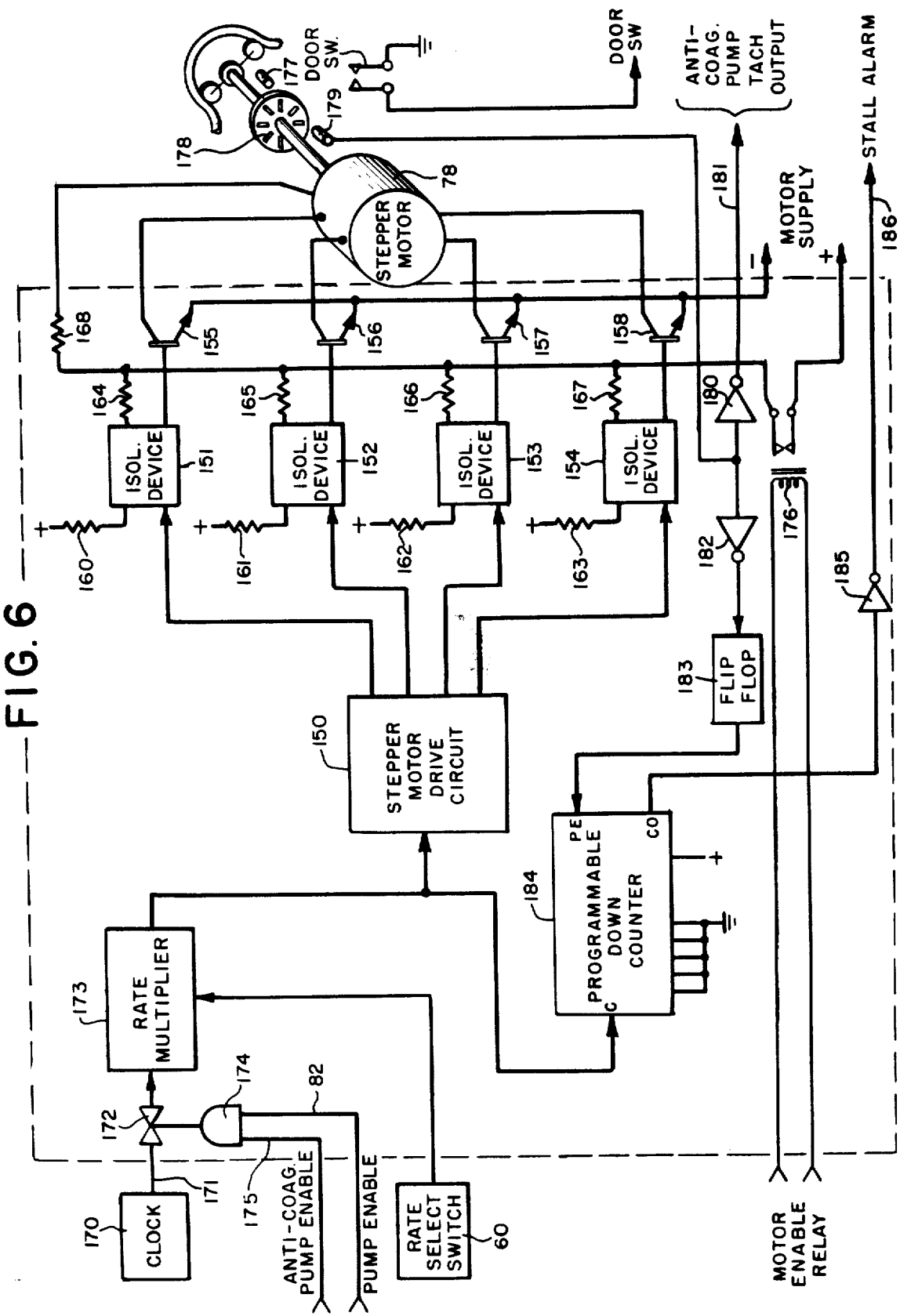
FIG. 6 is a functional block diagram partially in schematic form showing the anticoagulant pump motor control circuit of the plasmapheresis apparatus of FIG. 1.

Referring to FIG. 6, multi-phase drive signals are applied to the anticoagulant pump stepper motor 78 by a conventional stepper motor drive circuit 150. The signals are applied through respective ones of isolation devices 151–154 and transistors 155–158. Isolation devices 151–154, which may be conventional electro-optical devices, are connected by respective resistors 160–163 to a source of unidirectional operating current, and by respective resistors 164–167 to the motor power supply (not shown in FIG. 6). An additional resistor 168 supplies power to the stepper motor. Control pulses for initiating sequencing pulses from stepper motor drive circuit 150, and consequently each incremental rotation of the motor, are provided by a clock 170. Output pulses from the clock are applied through a distribution line 171 and an analog switch device 172 to a rate multiplier 173. Rate multiplier 173, which may be conventional in structure and operation, responds to an operator-selected rate set by switch 60 to provide a preselected rate multiplication to the applied clock pulses. This results in stepper motor drive circuits 150 being impulsed at a user-selected rate, and consequently the stepper motor 79 being driven at the desired rate.

Control over operation of stepper motor 79 is obtained by applying the pump enable control signal developed on line 82 by control circuit 81 to analog switch device 172 through an AND gate 174. The remaining input of AND gate 174 is connected to a separate pump enable control line 175 whereby control circuit 81 initiates anticoagulant pump operation only during the run and prime modes.

As an additional precaution against uncontrolled operation, current from the motor power source (not shown in FIG. 6) is applied to stepper motor 79 through the normally open contacts of a motor control relay 176. This relay, like similar relays in the WB and replacement motor control circuits 72 and 78, is energized by an enable signal on lines 132, 133 during normal operation of the system failsafe control circuit 84.

The anticoagulant pump tachometer 176 includes a light source 177, a slotted disc 178 and a photodetector 179. As disc 178 turns with motor 79, output pulses produced at photodetector 179 are supplied through a first inverter amplifier 180 to an anticoagulant tach output line 181 for application to failsafe circuit 84. Pulses are also supplied through a second inverter amplifier 182 to the input of a flip-flop 183 wherein they are conditioned for application to the parallel enable (PE) input of a programmable down counter. Upon application of each such tach output pulse, down counter 184 assumes a predetermined initial count, as determined by a hard-wired binary input. In the illustrated plasmapheresis apparatus a 64 is thus loaded.

Counter 184 is counted down from the parallel-loaded 64 initial counting state by output pulses from rate multiplier 173 until a zero count is reached, at which time the counter produces an output which is applied through an inverter amplifier 185 to the stall alarm line 186 associated with the anticoagulant pump.

As will be seen presently, this has the effect of signaling a stall condition to failsafe control circuit 83 and thereby stopping operation of the plasmapheresis apparatus. No stall alarm signal is produced as long as stepper motor 79 accomplishes sufficient movement to produce an output from photodetector 179 before 64 control pulses from rate multiplier 173 are applied to down counter 184, since 64 pulses are required before the down counter reaches a zero counting state. In this way, stall protection is provided for anticoagulant pump 40. A door switch 187 associated with the pump provides a door open signal on line 135 when the pump door is open.

Figure 7:
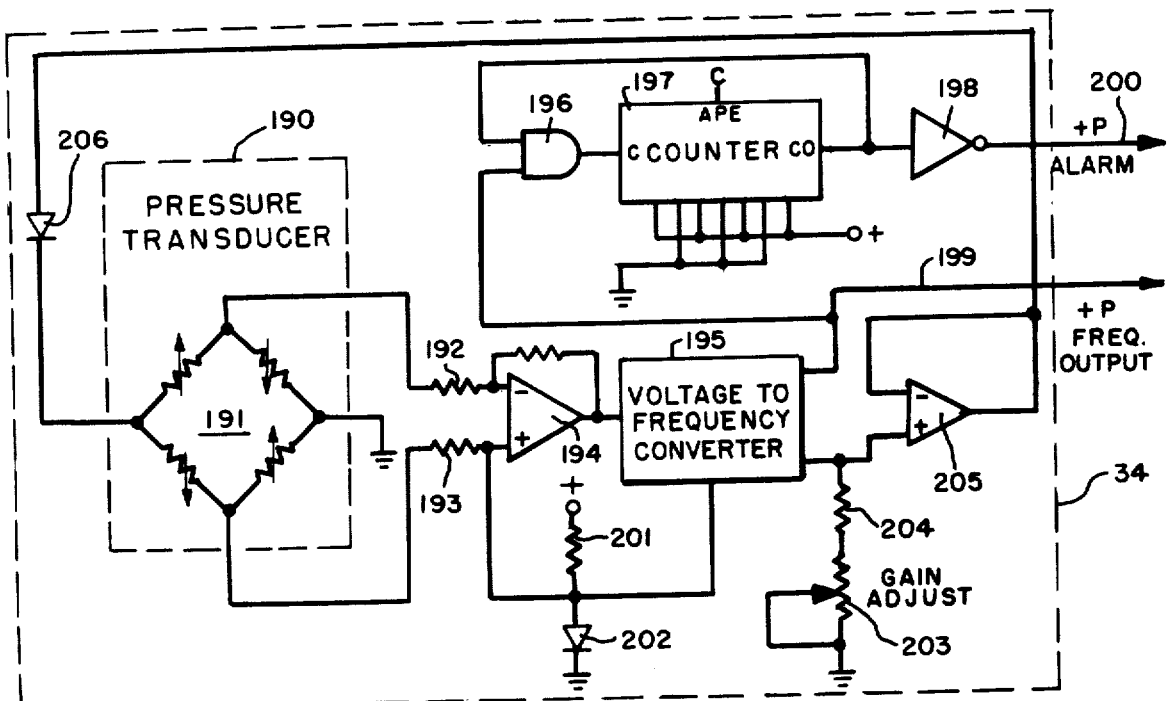
FIG. 7 is a functional block diagram partially in schematic form of the positive pressure monitor circuit of the plasmapheresis apparatus of FIG. 1.

Referring to FIG. 7, the positive pressure monitor circuit 34 includes a pressure transducer 190 of conventional construction. This transducer includes a tubing connection port (FIG. 1) which extends through the lower sloped panel of the apparatus housing to receive tubing segment 35 from flow set 30. Transducer 190, in accordance with conventional practice, forms a resistive bridge network 191 wherein the output resistance varies as a function of applied pressure. The output terminals of this bridge network are connected through respective resistors 192 and 193 to the inverting and non-inverting inputs of a differential amplifier 194. The output of this amplifier, which depends on the applied differential voltage, and hence on the pressure applied to transducer 190, is connected to a voltage-to-frequency converter 195. The output is also connected to the inverting input of the amplifier through a resistor to provide degenerative feedback.

Voltage-to-frequency converter 195 responds to the applied voltage to produce an output having a frequency related to the pressure present at transducer 190. This pressure-related signal is applied through an AND gate 196 to the clock input of a serial-parallel counter 197, and to a line 199 to provide a variable frequency pressure-indicative signal for use by display circuit 75. Upon the application of a clock pulse to the asynchronous parallel enable (APE) input of counter 197, the counter in accordance with conventional practice assumes an initial counting state equal to an applied hard-wired binary signal. Upon completion of the clock pulse the counter is counted down by each output pulse from converter 195 until reaching a zero count, at which time it produces an output signal. This signal is applied through an inverter amplifier 198 to a positive pressure alarm line 200 for application to control circuit 81. In addition, the output is applied to the remaining input of AND gate 196 to inhibit the application of further converter output pulses to the counter after completion of the count.

The effect of counter 197 is to establish a limit to the output frequency of converter 195 above which a positive pressure alarm is signaled. In practice, a count of 180 is hard-wired for loading into counter 197 once each second upon receipt of a one second clock pulse. If one count at the output of converter 195 is made to equal 1 millimeter of Hg, as in the illustrated plasmapheresis apparatus, then 180 mm Hg is established as the limit. If the frequency of the output of converter 195 is below 180, corresponding to a pressure less than 180mm Hg, then counter 197 does not reach a zero state and no positive pressure alarm is produced on line 200. Conversely, if the count exceeds 180, corresponding to a pressure in excess of 180 mm Hgl, counter 197 reaches a zero count and an alarm is produced.

To provide a necessary offset for converter 195 the non-inverting input of differential amplifier 194 and the reference input terminal of converter 195 are connected in a conventional manner to an offset voltage source comprising a resistor 201 and a diode 202 connected between ground and a source of current. Gain adjustment and temperature compensation are also provided in the supply circuit for transducer 190, which comprises a gain adjust potentiometer 203, a resistor 204, a differential amplifier 205 and a diode 206.

Figure 8:
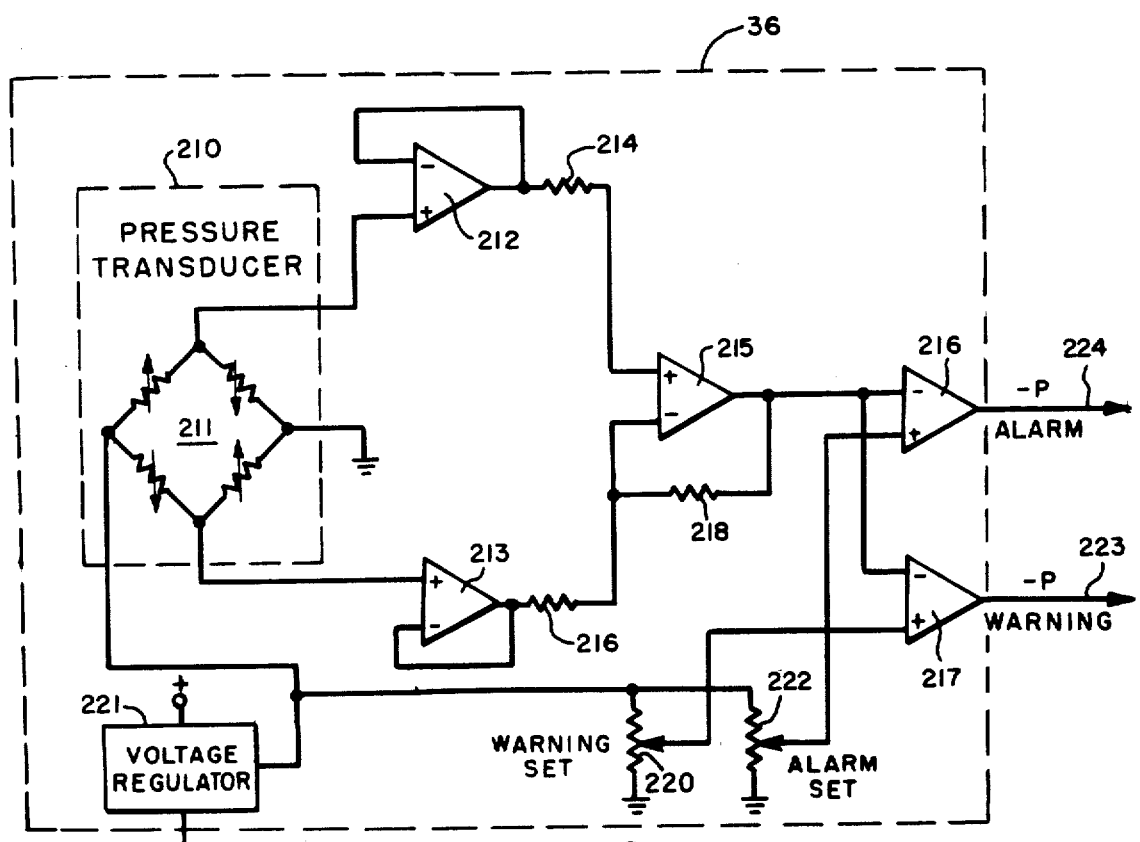
FIG. 8 is a functional block diagram partially in schematic form showing the negative pressure monitoring circuit of the plasmapheresis apparatus of FIG. 1.

Referring to FIG. 8, the negative pressure monitor circuit 36 includes a pressure transducer 210. This pressure transducer provides a resistive bridge network 211 having its output terminals connected to the non-inverting inputs of respective differential amplifiers 212 and 213. The output of amplifier 212 is connected to the inverting input of the amplifier, and through a resistor 214 to the non-inverting input of a third differential amplifier 215. The output of differential amplifier 213 is connected to the inverting input of the amplifier, and through a resistor 216 to the inverting input of differential amplifier 215. The output of differential amplifier 215 is connected directly to the inverting inputs of a pair of comparators 216 and 217, and through a resistor 218 back to the inverting input of the amplifier.

A reference voltage is applied to comparator 217 by a potentiometer 220 connected between a voltage regulator 221 and ground. Similarly, a reference voltage source is applied to differential amplifier 216 by means of a potentiometer 222 connected between the reference voltage source and ground. One input terminal of the resistive bridge network 211 is connected to the output of voltage regulator 221, and the other input terminal is connected to ground.

In operation, an output voltage is produced by pressure transducer 210 in a conventional manner. This voltage is applied through differential amplifiers 212 and 213 to the inverting and non-inverting inputs of differential amplifier 215 to produce an output voltage from that device indicative of applied pressure. This output voltage is compared by comparator 217 against a reference voltage established on the arm of resistor 220. When this reference voltage is exceeded, differential amplifier 217 produces an output which is recognized on a line 223 as a negative pressure warning by control circuit 81. Similarly, in differential amplifier 216 the applied output signal is compared against a reference established by potentiometer 222 and an alarm is produced on a line 224 when the reference is exceeded.

In practice, the reference set by potentiometer 222 is higher than that set by potentiometer 220, so that a warning output is produced prior to an alarm output. This is advantageous, since it allows the attendant, once aware of the impending low pressure alarm condition, to take remedial action, as by adjusting the interface between the donor and the system prior to an alarm level condition developing. As will be seen presently, the control system of the present invention facilitates such remedial action.

Figure 9:
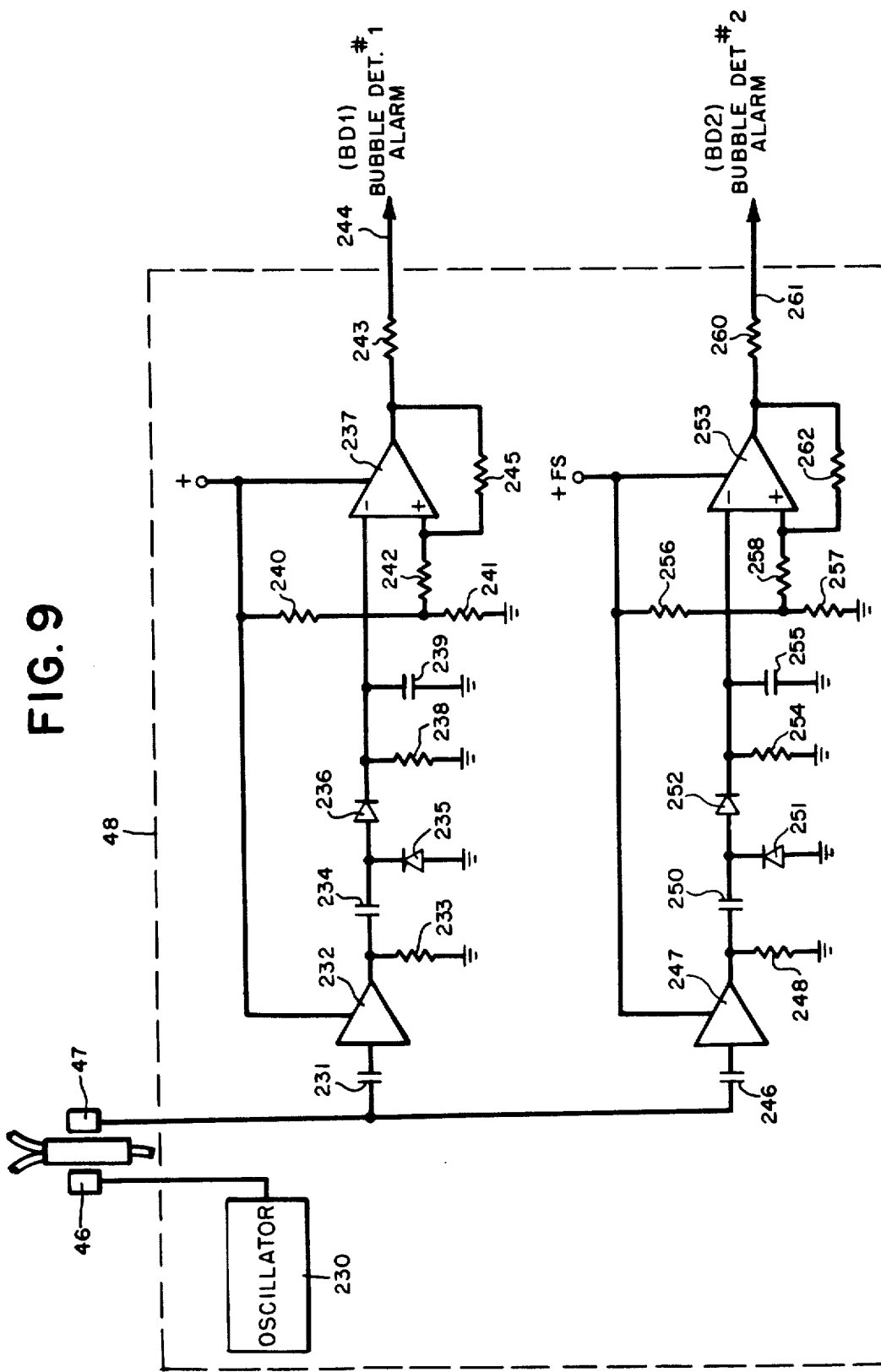
FIG. 9 is a simplified schematic diagram of the dual bubble detector circuit of the plasmapheresis apparatus of FIG. 1.

Referring to FIG. 9, the bubble detector circuit 48 includes first and second signal channels, providing first and second independent alarm outputs. A single ultrasonic oscillator 230 drives transducer 46. Ultrasonic energy passing through the fluid medium within the bubble detector chamber is received by transducer 47, which produces an AC output signal dependent on the intervening medium.

In the first signal channel, the output of transducer 47 is coupled through a capacitor 231 to the input of an amplifier 232. The output of this amplifier is connected through a resistor 233 to ground and through a capacitor 234 to a pair of diodes 235 and 236. Diode 235 is connected to ground to peak limit the output signal at a predetermined threshold level, and diode 236 is connected to the inverting input of a differential amplifier 237 and by a resistor 238 and a capacitor 239 to ground to provide peak detection for the output signal developed by amplifier 232.

A reference voltage is applied to the non-inverting input of comparator amplifier 237 by a voltage divider comprising resistors 240 and 241 connected between a system current source and ground. The junction of these resistors is coupled by a resistor 242 to the non-inverting input of the comparator. The output of the comparator is connected through a resistor 243 to a line 244 by which the occurrence of a bubble or fluid absence is signaled to the system control circuit 81. At the same time, the output of amplifier 237 is coupled back to the non-inverting input of the amplifier by a resistor 245 to provide regenerative feedback.

In operation, when the detected signal applied to comparator 237 falls below the reference level applied to the non-inverting input, the comparator provides an output (BD1) on line 244 which is recognized as the occurrence of a bubble or fluid absence. Amplifiers 232 and 237, as well as the voltage divider comprising resistors 240 and 241, are supplied by a positive polarity unidirectional current source derived from the main power supply of the apparatus. In contrast, as will be seen presently, the same components in the second bubble detector channel are supplied by current derived from a separate supply associated with failsafe control circuit 84.

The second bubble detector channel is identical in structure and operation to that of the first channel with the exception of utilizing the failsafe circuit power supply as its power source. The second channel includes a capacitor 246 which couples the output of transducer 47 to an amplifier 247. The output of this amplifier is connected to ground by a resistor 248 and through a capacitor 250 to diodes 251 and 252. Diode 251 is connected to ground to provide peak limiting action, and diode 252 is connected to the inverting input of a comparator amplifier 253 and to ground by the parallel combination of a resistor 254 and a capacitor 255. This provides peak detection for the received signal.

A reference voltage is developed at the non-inverting input of comparator 253 by a voltage divider comprising a pair of resistors 256 and 257. The juncture of these resistors is connected to the non-inverting input of the amplifier by a resistor 258. The output of comparator amplifier 253 is connected through a resistor 260 to a second alarm line 261 to provide a second bubble detector (BD2) alarm output for utilization by failsafe control circuit 84. The output of comparator 253 is also coupled by a resistor 262 to the non-inverting input of the device to provide regenerative feedback. The operation of the second bubble detector channel is identical to that of the first bubble detector channel.

Figure 10:
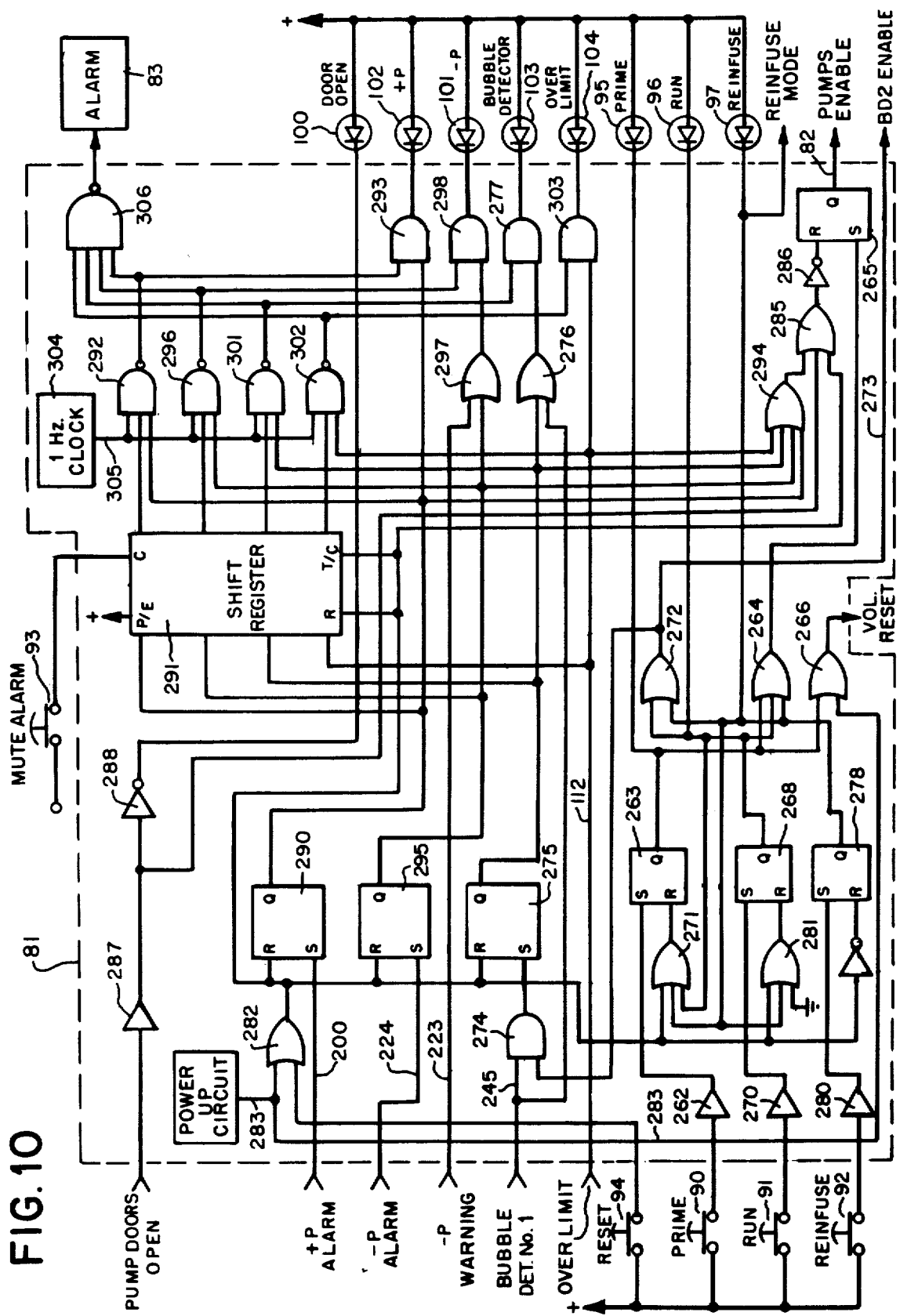
FIG. 10 is a simplified schematic diagram partially in functional block form of the control system of the plasmapheresis apparatus of FIG. 1.

Referring to FIG. 10, plasmapheresis apparatus 20 includes, in accordance with one aspect of the invention, a control circuit 81 which coordinates the operation of the pump motors 70, 76 and 79 and monitoring devices 34, 36 and 48 in discrete reset, prime, run and reinfuse operating modes, while providing in the event of abnormal system parameters an audible warning which can be reset by the operator while retaining a visual indication of the abnormal parameter. To initiate a plasmapheresis procedure the operator momentarily depresses the prime switch 90. This provides a signal through a non-inverting amplifier 262 to an RS-type mode control latch 263, which is conditioned by the signal to a reset mode. The output of latch 263 is applied to PRIME LED 95 to indicate that a prime mode has been selected. The output of the latch is also applied to one input of an OR gate 264. The output from this gate conditions an RS latch 265 to a set mode, which provides an output signal on the pump enable control line 82 to enable the three pumps of the apparatus in the manner previously described. The output of latch 263 is also applied to an OR gate 266, which provides a total volume reset signal on reset line 113 for utilization by the optional collection monitor and ratio control unit.

Upon completion of the prime procedure, run switch 91 is momentarily depressed. This causes a mode control latch 268 to be conditioned to its set mode through a non-inverting amplifier 270. The resulting output from latch 268 is applied to an OR gate 271 to provide a reset pulse for resetting latch 263, and to run LED 96 to provide a front panel indication that the apparatus is in the run mode. The output of latch 268 is also applied to an OR gate 272 and to a remaining input of OR gate 264. The resulting output of OR gate 272 provides an enabling signal for bubble detector No. 2 on a control line 273 for use by failsafe circuit 84, and an enabling input to an AND gate 274 associated with the set input of an RS-type alarm latch 275. The output from OR gate 264 operates in the manner previously described to condition latch 265 to a set state to provide a pump enabling signal on the first pump control line 82.

The remaining input of AND gate 274 is connected to the output of the No. 1 bubble detector (BD1) by line 244, so that upon the occurrence of a fluid absence in the run mode the BD1 output signal conditions RS latch 275 to a set mode. The BD1 output line 245 is also connected to an OR gate 276. The output of this gate is connected to one input of an AND gate 277. The output of AND gate 277 is connected to bubble trap LED 103, which provides a front panel indication of a fluid absence in the system. By reason of OR gate 276 and AND gate 277 LED 103 is caused to light when a fluid absence is detected, even if alarm latch 275 is not conditioned to its set mode by reason of the apparatus not being in the run mode and AND gate 274 being inhibited.

To begin the reinfuse mode the operator momentarily depresses switch 92 to condition an RS-type latch 278 to its set mode through a non-inverting amplifier 280. The resulting output from latch 278 is applied to an input of OR gate 264, to an input of OR gate 271, to an input of OR gate 272 and to reinfuse LED 97. LED 97 lights to indicate on control panel 55 that the reinfuse mode is in use. A signal is also provided on control line 175 to inhibit operation of the anticoagulant pump 40, as previously described. The output of latch 278 is also applied to one input of an OR gate 281 to reset latch 268, and to one input of OR gate 271 to reset latch 263. The output of OR gate 264 conditions latch 265 to its set mode, thus enabling the apparatus pumps through pump control line 82, in the manner previously described. The output of OR gate 272 enables the output of BD2 in failsafe control circuit 84, and enables AND gate 274 to the set input of latch 275, in the manner previously described.

To terminate operation the operator momentarily depresses switch 94, which applies a reset signal through an OR gate 282 to the reset inputs of the three mode control latches 263, 268 and 278 to reset these latches to their reset states. Consequently, the pump motors stop as the pump enable control signal is removed from motor control line 82. A reset signal generated on a reset line 283 during initial power-up of the apparatus by a power-up circuit 284 is applied to the other input of OR gate 282, and to the remaining input of OR gate 266 to cause a total volume reset signal on a reset line 113 at connector 67.

The output of OR gate 282 is applied to one input of an OR gate 285. The output of this gate is applied through an inverter amplifier 286 to the reset input of latch 265, through an inverter amplifier 289 to the reset input of latch 278, and to the remaining inputs of OR gates 271 and 281. Consequently, upon initial power-up of the apparatus latches 263, 268 and 278 are reset and RS latch 265 is conditioned to a reset mode, so that no pump enable signal is present on pump control line 82.

The pumps are also disabled upon one or more of the pump doors being opened, which it will be recalled result in a signal on the door open signal line 135. Within control circuit 81 the door open line 134 is connected through a noninverting amplifier 287 to another input of OR gate 285 to condition RS latch 265 to a reset state. Also, the output of amplifier 287 is applied through an inverter 288 to LED 100 to indicate on control panel 55 that a door is open.

In the event of a positive pressure alarm on line 200, which it will be recalled occurs should the pressure downline of the WB pump exceeds a predetermined level, an RS-type latch 290 is conditioned to a set state. The resulting output from latch 290 is applied to one input of a four section shift register 291, to one input of a NAND gate 292, to one input of an AND gate 293, and to one input of an OR gate 294. The output of AND gate 293 is connected to cell pressure LED (+P) 102, causing that device to light to signal a positive pressure alarm.

In the event of a negative pressure alarm on line 244, which occurs as a result of excessive negative pressure upline of the WB pump, an RS-type latch 295 is conditioned to a set mode. The resulting output from latch 295 is coupled to a second input of shift register 291, to one input of a NAND gate 296, to one input of an OR gate 297, and to one input of OR gate 294. The resulting output from OR gate 297 is applied through an AND gate 298 to inlet line (−P) LED 104, resulting in a negative pressure alarm on the apparatus control panel. The application of the signal to OR gate 294 results in latch 265 being conditioned to a reset state to terminate operation of the pump motors.

Receipt of a negative pressure warning on line 223 results in a signal being applied to the remaining input of OR gate 297. As a consequence, the output from OR gate 297 is applied through AND gate 298 to the inlet line (−P) LED 101 to provide a warning of an impending negative pressure alarm condition. Since the alarm condition occurs at a lower pressure level than the alarm condition, upon receipt of the warning the operator will have time to take corrective action before the occurrence of an alarm condition.

Upon occurrence of BD1 output latch 275 is conditioned to its set mode. The output of latch 275 is applied to a third input of shift register 291, to the remaining input of OR gate 276, to an input of NAND gate 301, and to an input of OR gate 294. OR gate 294 functions in response to the applied signal to condition RS latch 265 to a reset state to disable the pump motors. OR gate 276 provides an output through AND gate 277 which causes the bubble trap LED 103 to light.

One feature of the optional collection monitor and ratio control apparatus described in the previously identified copending applications of Arnold C. Bilstad and John T. Foley is that an over limit signal is generated upon the counters incorporated therein reaching excessively high counting states, as might result from a malfunction of the apparatus of the monitoring device. The resulting over limit signal is available on a line 112 at connector 67 for application to control circuit 81, wherein it is applied to a fourth input of shift register 291, to a NAND gate 302, to an input of AND gate 303 and to an input of OR gate 294. As a consequence, the output of AND gate 303 causes LED 105 to light to indicate an overlimit condition, and the motor control latch 265 is conditioned to a reset state to disable the pump motors.

In accordance with the invention, the outputs of alarm latches 290, 295 and 275, which comprise first latch means, and the overlimit control line 112, are connected to respective inputs of second latch means, in the form of the four input shift register 291. The same alarm signals are also each connected to one input of respective ones of the four NAND gates 292, 296, 301 and 302, which comprise part of an alarm circuit means. Shift register 291, which may be conventional in structure and operation, has four outputs. These outputs are each connected to a remaining input of respective ones of the NAND gates. The remaining inputs of NAND gates 301–304 are connected by a line 305 to a source of pulse signals, in this case a 1 hertz clock signal source 304. The outputs of NAND gates 292, 296, 301 and 302 are connected to remaining inputs of respective ones of AND gates 293, 298, 277 and 303, and to respective inputs of a four input NAND gate 306. The output of NAND gate 306 is connected to alarm 83.

The effect of the 1 hertz pulses on line 305 is to alternately enable and inhibit NAND gates 292, 296, 301 and 302 on a one second cyclical basis. As will be seen, this causes alarm 83 and the corresponding LED for an occurring fault to flash at a one second rate.

In a no-fault condition, the outputs of latches 290, 295 and 275, and the signal on overlimit line 112, are all logic low. This causes the NAND gates to be inhibited, with the result that each provides a logic high output. These outputs enable AND gates 293, 298, 277 and 303, allowing LED 101 to light upon receipt of a negative pressure warning on line 223, and LED 103 to light upon the absence of fluid at bubble detector 44. Since NAND gate 306 is enabled and provides a logic low output, alarm 82 is not activated. Since all inputs to OR gate 294 are low, no output is provided and latch 265 is conditioned according to the operating mode selected by mode control latches 262, 270 and 280.

In the event of an operating fault, such as a positive pressure alarm, latch 290 (or the latch appropriate to the particulat alarm) is conditioned to its set state. This produces a logic high which is applied to shift register 291, NAND gate 301, AND gate 293 and OR gate 294. OR gate 294 responds by conditioning latch 265 to its reset state to stop the pump motors. Shift register 291 does not immediately respond to the change in input, since a clock pulse is required before the register output will latch to the applied input state. Consequently, the output of the shift register remains high.

As a consequence of the change of state at the input of NAND gate 292 (two of the three inputs being logic high) gate 292 provides alternately high and low output states according to the state of line 305. This causes AND gate 293 to be alternately inhibited and enabled, so that with the steady logic high from latch 290 applied to its other input, it provides a flashing output for LED 103. At the same time, the periodic change of state of one of the inputs of NAND gate 306 results in an alternately logic high and logic low output being applied to alarm 83, so that the alarm pulsates at the clock rate.

The alarm and the LED associated with the alarm condition continue to pulsate until the operator momentarily depresses the mute alarm switch 93. This causes a momentary clock pulse to be applied to shift register 291. Upon receipt of the clock pulse, the shift register, in accordance with conventional operating principles, changes its output state to the complement of the input state. Consequently, the output of the register corresponding to the positive pressure monitor assumes a logic low, while the remaining outputs of the register remain logic high. The logic low, applied to NAND gate 292, causes that gate to be continuously inhibited. Since the output of NAND gate 292 is logic high, the output of NAND gate 306 is a steady logic low which does not activate alarm 83. Also, AND gate 293 is now continuously enabled so that LED 103 is steadily illuminated.

Thus, an initial alarm condition results in a pulsating aural alarm and a flashing visual alarm. The operator, having noted an aural alarm condition, can silence the alarm and change the lamp to steady by merely pressing the mute switch. This is a great advantage in often busy clinical and hospital environments, where it may not be possible to immediately remedy an alarm situation, but yet it is necessary to automatically provide a reminder of the alarm having been sounded.

The operation of the alarm feature of the control circuit is identical for the negative pressure alarm, the bubble detector alarm, and the overlimit alarm. In each case a corresponding lamp flashes and the alarm sounds intermittently until the mute alarm switch 93 is depressed, after which the alarm is muted and the lamp lights continuously.

It will be noted that BD1 is enabled as an alarm condition only when the apparatus is in its run or reinfuse modes. This is to prevent the bubble detector from providing an alarm which terminates operation during the prime mode, when air in the lines is normal. However, OR gate 276 allows the bubble trap LED 102 to light during the prime mode to indicate that the bubble detector is operative.

Figure 11:
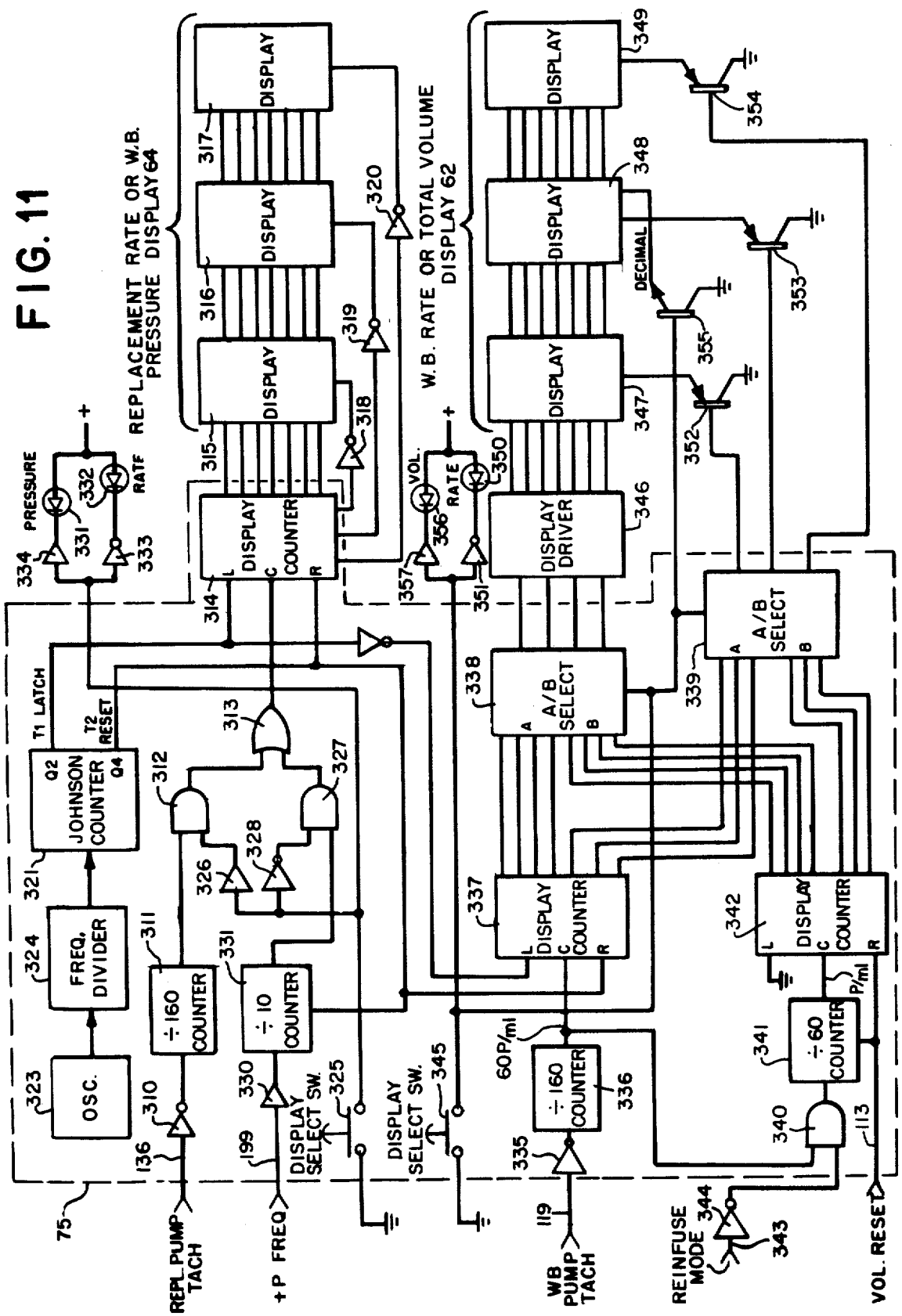
FIG. 11 is a simplified schematic diagram partially in functional block form showing the display system of the plasmapheresis apparatus of FIG. 1.

Referring to FIG. 11, within display circuit 75 the pulses from the replacement motor pump tach 77 on line 136 are applied through an inverter 310 and counter 311 to an AND gate 312. Counter 311 is set to divide by a factor of 160, producing one output pulse for each 160 input pulses from inverter 310. If AND gate 312 is enabled, the frequency-divided pulses are applied through an OR gate 313 to the clock input of a display counter 314. Counter 314, which may be conventional in structure and operation, responds to the applied pulses to accumulate a count indicative of the volume in milliliters pumped by replacement pump 52. At the end of the measurement period, in this case one second, a latch pulse is applied to counter 314 to cause the counter in a conventional manner to assume the accumulated count and provide an appropriate driving signal for a trio of associated seven segment display panels 315-317, which comprise readout 64 on panel 55. Appropriate strobe pulses for enabling the displays are provided by counter 314 through respective ones of inverter amplifiers 318-320.

Following the latch pulse, after the display counter has assumed at its output the previously accumulated count, the accumulated count is reset by a reset clock pulse ($T_2$) applied to the reset input of the counter. This reset pulse, and a corresponding latch pulse ($T_1$), are developed at a one second repetition rate by a Johnson counter 321. This counter is clocked by a one hertz signal obtained from a clock circuit, which includes an oscillator 323 and frequency divider 324 of conventional design. Since alternate outputs of the Johnson counter are utilized, the latch pulse leads and is distinct from the reset pulse, so that counter 314 completes its latch function before it begins its reset function, thus assuring that the counter will display the preceding count during the subsequent one second counting interval.

The replacement rate display 64 can be alternatively switched to a display of fluid pressure at the output of the WB pump by momentary actuation of a push button switch 325. This causes AND gate 312 to be inhibited through a non-inverting amplifier 326, and an AND gate 327 to be enabled through an inverter 328. As a result, the variable frequency positive pressure pulses at 10 hertz per millimeter of mercury developed on line 199 by the positive pressure monitor 34 are supplied to display counter 314 through a non-inverting amplifier 330, a divide-by-ten counter 331, and OR gate 313. Since counter 314 continues to be reset once each second, the counter in effect measures the frequency in hertz per second, which translates directly to millimeters of mercury. An indication is given of the display selected for readout 64 by LED indicators 331 and 332. When display select switch 325 is not actuated, as during normal operating conditions, LED 332, indicating a reinfuse rate reading, is powered through inverting amplifier 333. When display select switch 325 is actuated, LED 331, indicating a pressure reading, is illuminated through non-inverting amplifier 334.

The whole blood flow rate, and the total volume of whole blood processed, may be similarly read on readout 62. To this end, the output of the WB pump tach 71, on line 119, is applied through an inverter 335 to the input of a divide-by-160 counter 336. The output of this counter, which comprises 60 pulses per milliliter pumped by the WB pump, is applied to the clock input of a latch-type display counter 337. This counter, which may be conventional in structure and operation, counts the applied pulses until a $T_1$ (latch) clock pulse is applied to its latch input through an inverter 338, at which time the accumulated count is latched and a corresponding output is provided. Following a short delay, a $T_2$ (reset) clock pulse is applied to the reset input of the counter to return the counter to zero in preparation for another counting cycle. Consequently, the output of the counter may be read as the whole blood flow rate.

The BCD data output of counter 337, which comprises a four digit BCD signal, is applied to the A input of a first A/B select switch 338, which functions in a conventional manner to select one of two applied BCD signals depending on an applied control signal. The strobe output of the counter is applied to the A input of a second A/B select switch 339.

The output of counter 336 is also applied through an AND gate 340 and a divide-by-60 counter 341 to the clock input of a display counter 342. AND gate 340 is enabled when the plasmapheresis apparatus is not in its reinfuse mode by a control signal developed on line 175 by control circuit 81 and applied to the remaining input of AND gate 340 through an inverter 344. When plasmapheresis apparatus 20 is operating in the reinfuse mode, the signal on control line 343 through inverter 344 inhibits AND gate 340 to prevent the application of whole blood pump tach pulses to counter 342. The output pulses of counter 336, each representing the pumping of one milliliter of whole blood, are accumulated by counter 342 on a real time basis, the latch input of the counter being connected to ground. The counter continues to accumulate pulses until reset by application of a reset pulse on line 113. Consequently, the count in counter 342 represents the total volume of whole blood pumped over the time interval between reset pulses. The BCD data output of counter 342 is applied to the B input of A/B select switch 338, and the strobe output of the counter is applied to the B input of A/B select switch 339.

A/B select switches 338 and 339 are controlled by a control signal developed by a display select switch 345. In the normal unactuated position of select switch 345 A/B select switches 338 and 339 select the A inputs. This causes the four digit data output signals of display counter 337 to be applied to a conventional display driver 346, which converts the signal to a seven digit signal for driving a trio of display panels 347-349. These display panels comprise the digital readout 62 on control panel 55. Necessary strobe signals are also provided to the display panels by counter 337 through A/B select switch 339 and respective display control transistors 352-355. A rate indicator LED 350 is lit during WB rate display by the circuit display select switch 345 through inverting amplifier 351.

Upon actuation of the display select switch, A/B select switches 338 and 339 select the B inputs and the four digit data output signal from counter 342 is applied through display driver 338 to display panels 347-349 to provide a display of total volume processed. At the same time, strobe signals from counter 342 are applied to the display panels 347-349 through respective ones of transistors 352-354 and a decimal point is provided in display panel 348 by means of a transistor 355 rendered conductive by closure of switch 345. A volume processed LED indicator 356 is lit through a non-inverting amplifier 357 when switch 345 is actuated. Thus, depending on the position of display select switch 345, readout 62 may indicate either the whole blood rate, in milliliters per minute, or total whole blood volume processed, in liters.

Referring to FIG. 12, plasmapheresis apparatus 20 includes a failsafe circuit for terminating operation of the apparatus in the event of a failure in the control system. Referring to FIG. 12, within failsafe circuit 84 the anticoagulant pump stall signal on line 186 is applied through an inverter amplifier 360 to an isolation network 361, which provides electrical isolation between the circuits of the stepper motor of the anticoagulant pump, and the failsafe circuitry. The input end of the network is connected to the regulated unidirectional current source provided for the other circuits of the system, and the output end is connected to a separate power source 362 (+FS) within the failsafe circuit. This power source receives operating power from the motor power supply 359, which supplies motors 70, 76 and 79.

The output of network 361 is applied to one input of an OR gate 363. The WB pump motor overspeed/stall output, on line 128, is applied through a non-inverting amplifier 364 to a second input of OR gate 363. Similarly, the output of the replacement pump overspeed/stall circuit on line 135 is applied through a non-inverting amplifier 365 to the remaining input of OR gate 363. The output of OR gate 363, which is present upon the occurrence of a stall condition in one or more of the three system pump motors, is applied to one input of an OR gate 366. The output of emergency stop switch 98, available on a control line 367, is applied through an inverter amplifier 368 to another input of OR gate 366. The output of OR gate 366 is applied to the clock input of JK-type flip-flop 369. The Q output of flip-flop 369 is connected directly to the failsafe motor stop line 85 to inhibit the operation of all motors upon the occurrence of a clock pulse at the input of flip-flop 369. The Q output of flip-flop 369 is also connected through an inverter 370 to the emergency stop LED 105, and to an aural alarm 371 of conventional structure and operation. The $\overline{Q}$ output of flip-flop 369 is connected through an inverter amplifier 372 to motor relay line 132 of the failsafe system. The other motor relay line 133 is connected to the positive polarity output of the motor power supply. As previously described, this power supply also supplies operating power to the various pump motors of the plasmapheresis apparatus, and to the regulated power supply 362 of the failsafe system.

In addition to monitoring the stall and overspeed detection circuits of the three system motors, failsafe circuit 84 also checks for actual motion of the motors in the event of a bubble or fluid absence being detected. To this end, the output of the WB pump tach on line 119 is fed through an inverter amplifier 374 to an isolation network 375, which provides isolation in a conventional manner between the apparatus low voltage supply utilized by the WB motor control circuit and the power supply 362 of the failsafe system. The output of isolation network 375 is applied to a first JK-type flip-flop 376, which changes state in response to each applied tach pulse.

Replacement pump tach pulses on line 136 are applied through an inverter amplifier 377 and an isolation network 378 to the clock input of a second JK-type flip-flop 379, which changes state in response to each applied tach pulse. Similarly, the anticoagulant pump tach pulses on line 181 are applied through an inverter amplifier 380 and an isolation network 381 to the clock input of a third JK-type flip-flop 382, which changes state in response to each applied tach pulse.

The outputs of flip-flops 376, 379 and 382 are applied to respective inputs of a three input OR gate 383, causing the output of the gate to change state periodically as tach pulses are applied to any one of the three flip-flops. The output of OR gate 383 is applied through an inverter amplifier 384 to the parallel/serial (P/S) control input of a shift register 385. This register, which comprises a series-parallel counter which is normally in a parallel mode, is conditioned to a serial mode upon the application of an input signal on its parallel/serial enable input. Once enabled in its serial mode, shift register 385 provides an output following the application of four clock pulses to its clock input.

In normal operation shift register 385 is inhibited from operating in its serial mode by a reset signal applied to its reset input by bubble detector No. 2 (BD2) through a non-inverting amplifier 386 and a NAND gate 387. NAND gate 387 is enabled by a control signal present on control line 273 whenever the run or reinfuse modes are selected, as provided by control circuit 81. The signal on line 273 is fed through an isolation network 388 to the remaining input of NAND gate 387. The output of BD2, being logic low except upon the occurrence of a fluid absence, normally prevents the output of gate 387 from assuming other than a logic high. However, if the output of BD2 becomes logic high, and if the bubble detector enable line 273 is also logic high, NAND gate 387 produces a logic low which removes the reset signal from shift register 385.

If any one of the system tachometers is providing output pulses at the time the reset pulse is removed by the occurrence of a bubble, shift register 385 is conditioned to a serial mode and begins to count. After the application of four clock pulses to the clock input of the register, an output is produced by the register which is applied to the remaining input of OR gate 366. This conditions flip-flop 269 to its alarm state, and operation of the apparatus is interrupted.

To insure that flip-flop 269 will always be in a reset state in the absence of a fault condition, a power-up circuit 389 is provided to supply an initial reset pulse to the reset input of flip-flop 369 upon power-up of the apparatus. The necessary clock pulses for shift register 385 are supplied at a one second rate by a conventional clock circuit 390. This clock circuit may include conventional oscillator and frequency divider circuits (not shown) for deriving the desired one second clock signal. The output of clock 390 is also applied through a pair of serially-connected inverters 391 and 392 to the reset inputs of flip-flops 376, 379 and 382 to reset these devices following each clock period.

Thus, following occurrence of a bubble or fluid absence at the second bubble detector, if any one of the pumps continues to run for more than four seconds a stop sequence is initiated which removes all operating power from the pumps. Once this condition has occurred, it can only be reset and operation resumed by removing all power from the plasmapheresis apparatus so that powerup circuit 390 resets flip-flop 385.

While the invention has been shown in conjunction with plasmapheresis apparatus, it will be appreciated that the invention can also be utilized in other blood fractionation procedures where components other than plasma are separated and collected.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

We claim:

1. In a blood fractionation apparatus operable in conjunction with a disposable flow system for separating and collecting a blood fraction from whole blood, and including at least one motor-driven pump for conveying blood through the flow system, and a monitoring device providing an alarm output response to an abnormal condition in the system, a control circuit comprising, in combination:

a flip-flop responsive to a momentary alarm output from said monitoring device for producing a first alarm control signal;
   a latch register responsive to the occurrence of said control signal for producing a second alarm control signal upon application of a latch signal;
   aural alarm means;
   visual alarm means;
   alarm control circuit means responsive to said first alarm control signal for activating said aural and visual alarm means, and responsive to said second alarm control signal for inhibiting only said aural alarm means; and
   user-actuated switch means for applying a latch control signal to said latch register to cancel said aural alarm without cancelling said visual alarm.

2. A blood fractionation apparatus as defined in claim 1 wherein said flip-flop is an RS type flip-flop.

3. A blood fractionation apparatus as defined in claim 1 wherein said alarm control circuit means intermittently actuate said aural and visual alarm means prior to actuation of said latch register.

4. A blood fractionation apparatus as defined in claim 1 wherein said alarm control circuit means include a first AND gate having one input connected to the output of said flip-flop, and another input connected to the output of said latch register, and an output connected to said aural alarm means.

5. A blood fractionation apparatus as defined in claim 4 wherein said alarm control circuit includes a second AND gate having one input connected to the output of said flip-flop, another input connected to the output of said first AND gate, and an output connected to said visual alarm.

6. A blood fractionation apparatus as defined in claim 5 including a source of intermittent control signals, and wherein said first AND gate includes an input coupled to said source of intermittent control signals whereby said aural and visual alarms are intermittently operated in the presence of said first alarm control signal and in the absence of said second alarm control signal.

7. In a blood fractionation apparatus operable in conjunction with a disposable flow system for separating and collecting a blood fraction from whole blood, and including at least one motor-driven pump for conveying blood through the flow system, and a monitoring device providing an alarm output in response to an abnormal condition in the system, a control circuit comprising, in combination:

a flip-flop responsive to a momentary alarm output from said monitoring device for producing a first alarm control signal;
   a latch register responsive to the occurrence of said first alarm control signal for producing a second alarm control signal upon application of a latch control signal;
   aural alarm means;
   visual alarm means;
   alarm control means including a first AND gate having inputs connected to the outputs of said flip-flop and said latch register, and an output connected to said aural alarm, and a second AND gate having inputs connected to the outputs of said flip-flop and said first AND gate, and an output connected to said visual alarm, for activating said aural and visual alarm means in response to said first alarm control signal, and only said visual alarm control signal in the presence of said second alarm control signal; and user-actuated switch means for applying a latch control signal to said latch register to cancel said aural alarm without cancelling said visual alarm.

8. A blood fractionation apparatus as defined in claim 7 wherein said first AND gate has a third input, and wherein said apparatus includes a pulse source for applying pulses to said first AND gate to intermittently sound said alarm.

9. A blood fractionation apparatus as defined in claim 7 wherein said second alarm control signal is of opposite binary gender to said first alarm control signal.

* * * * *